(12) United States Patent
Allen

(10) Patent No.: US 8,227,608 B2
(45) Date of Patent: Jul. 24, 2012

(54) PROCESSES FOR INCREASING THE YIELD OF OPIATE ALKALOID DERIVATIVES

(75) Inventor: Brenda E. Allen, Fieldon, IL (US)

(73) Assignee: Mallinckrodt LLC, Hazelwood, MO (US)

( * ) Notice: Subject to any disclaimer, the term of this patent is extended or adjusted under 35 U.S.C. 154(b) by 445 days.

(21) Appl. No.: 12/586,842

(22) Filed: Sep. 29, 2009

(65) Prior Publication Data

US 2010/0081814 A1  Apr. 1, 2010

Related U.S. Application Data

(60) Provisional application No. 61/194,680, filed on Sep. 30, 2008.

(51) Int. Cl.
*C07D 489/12* (2006.01)
*C07D 489/10* (2006.01)

(52) U.S. Cl. ............................................. 546/39; 546/38
(58) Field of Classification Search ................... 546/39, 546/38
See application file for complete search history.

(56) References Cited

U.S. PATENT DOCUMENTS
2005/0164358 A1  7/2005  Carnell et al.

FOREIGN PATENT DOCUMENTS
CN   101 260 111 A   9/2008
WO   WO 2006/025710   3/2006

OTHER PUBLICATIONS

"Synthesis of N-Substituted 7B-Diprenorphine Derivatives", Synthetic Comm., 25(6), 1995, pp. 829-848.

*Primary Examiner* — Charanjit Aulakh

(57) ABSTRACT

The present invention provides processes for the production of opiate alkaloids. In particular, the present invention provides processes for recycling impurities into useful intermediates during the synthesis of opiate alkaloids.

23 Claims, No Drawings

PROCESSES FOR INCREASING THE YIELD OF OPIATE ALKALOID DERIVATIVES

CROSS REFERENCE TO RELATED APPLICATIONS

This application claims priority from U.S. Provisional Application No. 61/194,680, filed on Sep. 30, 2008, which is hereby incorporated by reference in its entirety.

FIELD OF THE INVENTION

The present invention generally relates to processes for synthesis of opiate alkaloids. In particular, the present invention provides processes for recycling impurities into useful intermediates during the synthesis of opiate alkaloids.

BACKGROUND OF THE INVENTION

Thebaine is an opiate alkaloid. While thebaine is not used therapeutically itself, it can be converted industrially into a variety of therapeutically important opiate alkaloids including oxycodone, oxymorphone, nalbuphine, naloxone, naltrexone, diprenorphine, buprenorphine and etorphine. Buprenorphine, for example, is a thebaine derivative with powerful analgesia approximately twenty-five to forty times as potent as morphine, and is indicated for the treatment of moderate to severe chronic pain or for the treatment of opiate addiction.

A series of chemical reactions convert thebaine to 3-O-methyl-N-cyano-buprenorphine (whose chemical name is 6,14-ethenomorphinan-17-carbonitrile, 4,5-epoxy-18,19-dihydro-7-(1-hydroxy-1,2,2-trimethylpropyl)-3,6-dimethoxy-). A hydrolysis reaction then converts 3-O-methyl-N-cyano-buprenorphine to norbuprenorphine (whose chemical name is 6,14-ethenomorphinan-7-methanol, α-(1,1-dimethylethyl)-4,5-epoxy-18,19-dihydro-3-hydroxy-6-methoxy-α-methyl-). During the hydrolysis reaction, however, the partially hydrolyzed intermediate, 3-O-methyl-norbuprenorphine, is formed. 3-O-methyl-norbuprenorphine is an impurity that has to be removed to achieve the highest purity and yield of the product, norbuprenorphine. Since the levels of the 3-O-methyl-norbuprenorphine impurity can be as high as 10%, this step of the process significantly reduces the final yield of buprenorphine. A need therefore exists for a process to reduce the formation of 3-O-methyl-norbuprenorphine or recycle it back into the buprenorphine production process.

SUMMARY OF THE INVENTION

The present invention provides a process for the conversion of 3-O-methyl-norbuprenorphine into norbuprenorphine and a process for recycling 3-O-methyl-norbuprenorphine back into the production of buprenorphine. Accordingly, one aspect of the invention provides for a process for the preparation of a compound comprising Formula (II). The process comprises contacting a compound comprising Formula (I) with a hydrolysis agent to form the compound comprising Formula (II):

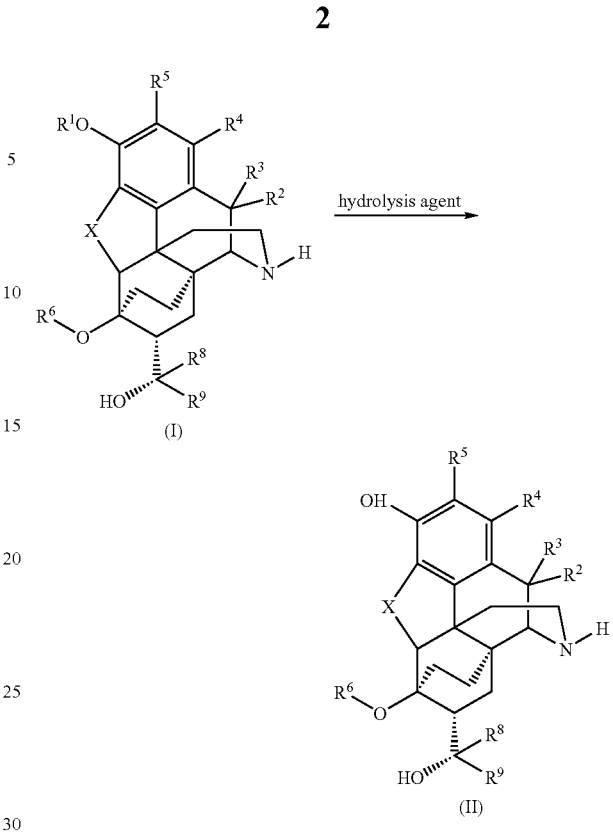

wherein:
$R^1$, $R^7$, $R^8$, and $R^9$ are independently selected from the group consisting of hydrocarbyl and substituted hydrocarbyl;
$R^2$ and $R^3$ are independently selected from the group consisting of hydrogen, hydrocarbyl, and substituted hydrocarbyl;
$R^4$ and $R^5$ are independently selected from the group consisting of hydrogen, hydrocarbyl, substituted hydrocarbyl, halogen, {—}OH, {—}NH$_2$, {—}SH, {—}SR$^7$, and {—}OR$^7$;
$R^6$ is independently selected from the group consisting of hydrogen, a protecting group, hydrocarbyl, and substituted hydrocarbyl; and
X is a heteroatom.

Another aspect of the invention encompasses a process for the preparation of a compound comprising Formula (IIa). The process comprises contacting a compound comprising Formula (Ia) with a hydrolysis agent to form the compound comprising Formula (IIa):

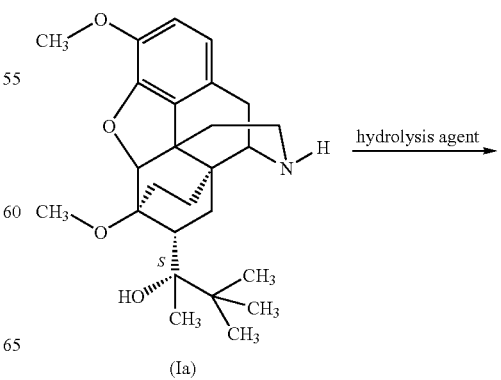

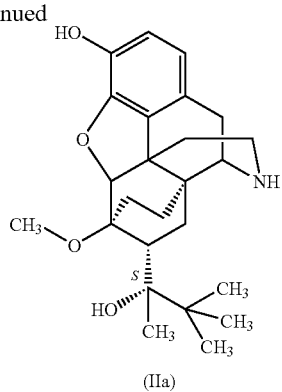

(IIa)

A further aspect of the invention provides process for the preparation of a compound comprising Formula (II). The process comprises (a) contacting a compound comprising Formula (Ib) with a first hydrolysis agent to form the compound comprising Formula (II) and a compound comprising Formula (I), and (b) isolating the compound comprising Formula (I) and contacting it with a second hydrolysis agent to form additional amounts of the compound comprising Formula (II):

wherein:
R$^1$, R$^7$, R$^8$, and R$^9$ are independently selected from the group consisting of hydrocarbyl and substituted hydrocarbyl;
R$^2$ and R$^3$ are independently selected from the group consisting of hydrogen, hydrocarbyl, and substituted hydrocarbyl;
R$^4$ and R$^5$ are independently selected from the group consisting of hydrogen, hydrocarbyl, substituted hydrocarbyl, halogen, {—}OH, {—}NH$_2$, {—}SH, {—}SR$^7$, and {—}OR$^7$;
R$^6$ is independently selected from the group consisting of hydrogen, a protecting group, hydrocarbyl, and substituted hydrocarbyl; and
X is a heteroatom.

Still another aspect of the invention encompasses a process for the preparation of a compound comprising Formula (IIa). The process comprises (a) contacting a compound comprising Formula (Ic) with a first hydrolysis agent to form the compound comprising Formula (IIa) and a compound comprising Formula (Ia), and (b) isolating the compound comprising Formula (Ia) and contacting it with a second hydrolysis agent to form additional amounts of the compound comprising Formula (IIa):

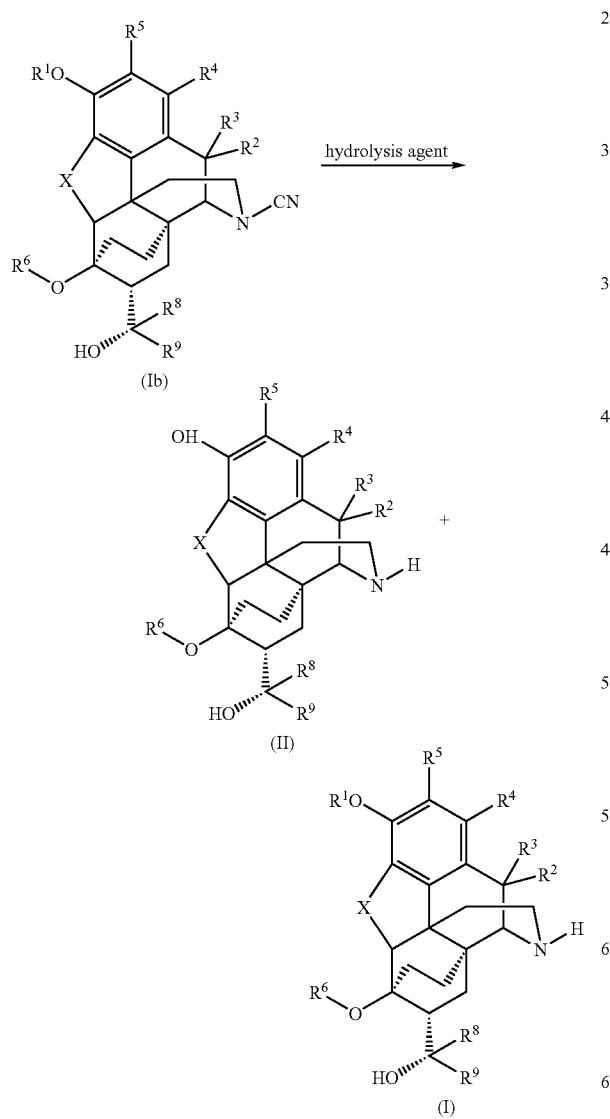

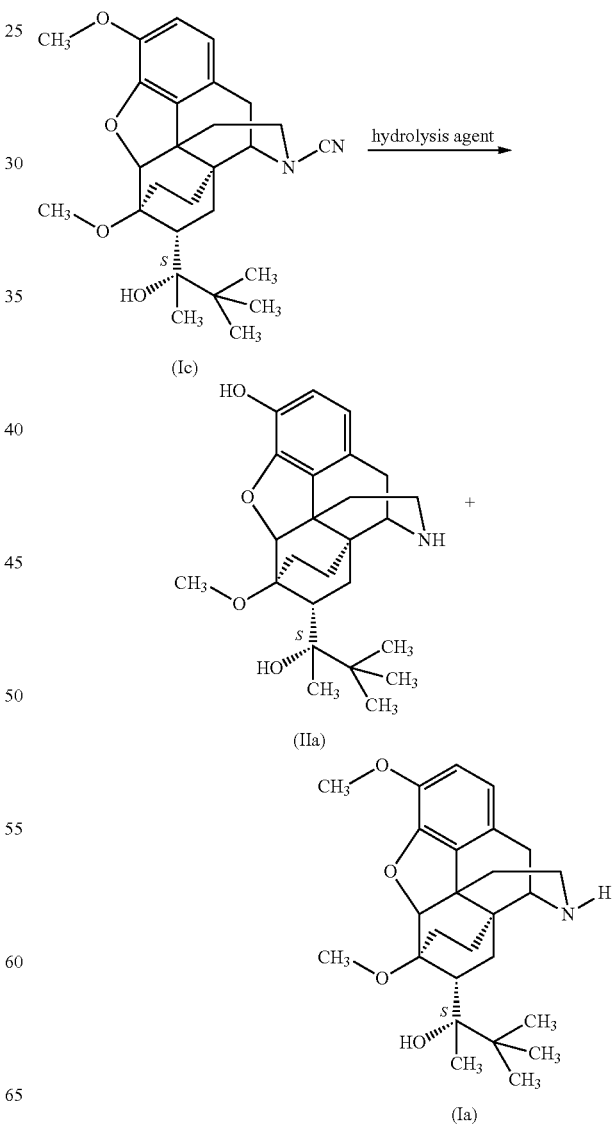

Additional aspects and iterations of the invention are described in more detail below.

DETAILED DESCRIPTION

It has been discovered that 3-O-methyl-norbuprenorphine may be used as starting material to produce norbuprenorphine. This discovery provides a way to increase the overall yield of norbuprenorphine during its synthesis from thebaine. Specifically, the by-product, 3-O-methyl-norbuprenorphine, formed during the hydrolysis of 3-O-methyl-N-cyano-buprenorphine may be isolated, converted to norbuprenorphine, and then combined with the previously produced norbuprenorphine. This recycling process thereby increases the yield of norbuprenorphine, and ultimately, increases the yield of buprenorphine. Provided herein, therefore, are processes for the synthesis of 3-hydroxy opiate alkaloids from 3-substituted and/or 3-substituted-N-cyano opiate alkaloids.

(I) Synthesis of Compounds Comprising Formula (II) from Compounds Comprising Formula (I One aspect of the invention provides a process for the conversion of a 3-O-substituted opiate alkaloid into a 3-hydroxy opiate alkaloid. In particular, the process comprises the hydrolysis of a 3-O-substituted opiate alkaloid comprising Formula (I) to produce a 3-hydroxy opiate alkaloid comprising Formula (II). For the purposes of illustration, Reaction Scheme 1 depicts the formation of compound comprising Formula (II) in accordance with this aspect of the invention.

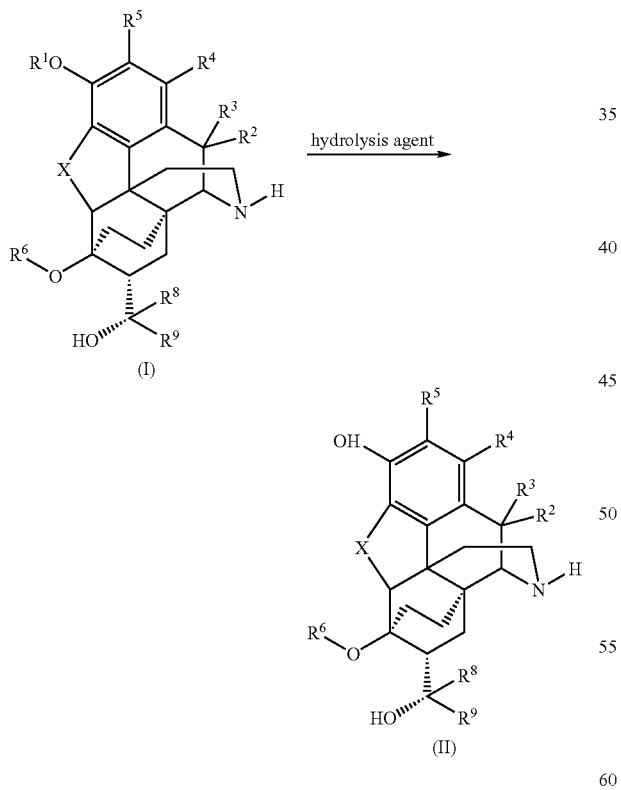

wherein:
R$^1$, R$^7$, R$^8$, and R$^9$ are independently selected from the group consisting of hydrocarbyl and substituted hydrocarbyl;
R$^2$ and R$^3$ are independently selected from the group consisting of hydrogen, hydrocarbyl, and substituted hydrocarbyl;
R$^4$ and R$^5$ are independently selected from the group consisting of hydrogen, hydrocarbyl, substituted hydrocarbyl, halogen, {—}OH, {—}SH, {—}SR$^7$, and {—}OR$^7$;
R$^6$ is independently selected from the group consisting of hydrogen, a protecting group, hydrocarbyl, and substituted hydrocarbyl; and
X is a heteroatom, In one embodiment of the process, R$^1$, R$^6$, R$^8$, and R$^9$ are alkyl or substituted alkyl, and X is oxygen. In an iteration of this embodiment, R$^2$, R$^3$, R$^4$, and R$^5$ are hydrogen. In another embodiment, R$^2$, R$^3$, R$^4$, and R$^5$ are hydrogen, and X is oxygen. In yet another embodiment, R$^1$ and R$^6$ are methyl. In an iteration of this embodiment, X is oxygen. In a further iteration, R$^6$ and R$^9$ are alkyl or substituted alkyl.

In an exemplary embodiment, the compound comprising Formula (II) is norbuprenorphine comprising Formula (IIa):

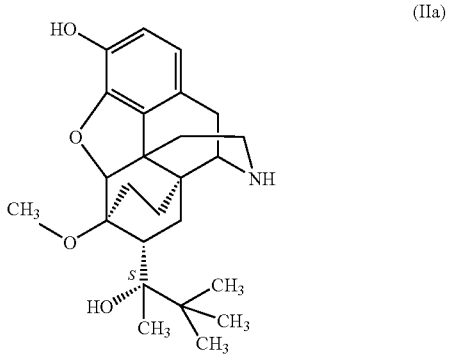

(a) Reaction Mixture

The process comprises forming a reaction mixture that includes a compound comprising Formula (I). A variety of compounds comprising Formula (I) are suitable for use in the process, In one embodiment of the process, for the compound comprising Formula (I), R$^1$, R$^6$, R$^8$, and R$^9$ are alkyl or substituted alkyl, and X is oxygen. In an iteration of this embodiment, R$^2$, R$^3$, R$^4$, and R$^5$ are hydrogen. In another embodiment, R$^2$, R$^3$, R$^4$, and R$^5$ are hydrogen, and X is oxygen. In yet another embodiment, R$^1$ and R$^6$ are methyl, In an iteration of this embodiment, X is oxygen. In a further iteration, R$^8$ and R$^9$ are alkyl or substituted alkyl.

In an exemplary embodiment of the process, the compound comprising Formula (I) is 3-O-methyl-norbuprenorphine comprising Formula (Ia):

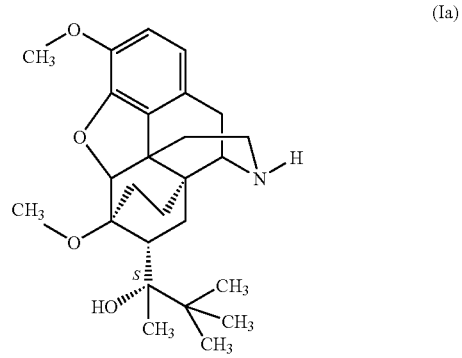

In addition to the compound comprising Formula (I) or (Ia), the reaction mixture also includes a hydrolysis agent. Typically, the hydrolysis agent is a compound having a pKa greater than about 12.0. Non-limiting examples of suitable compounds include group 1 and group 2 salts of hydroxides (such as, for example, KOH and Ca(OH)$_2$ and the like); and metal oxides (such as, for example, magnesium oxide, calcium oxide, and the like). In a preferred embodiment the hydrolysis agent may be a hydroxide of a group 1 or group 2 metal. In an exemplary embodiment, the hydrolysis agent may be potassium hydroxide. The molar ratio of the compound comprising Formula (I) or (Ia) to the hydrolysis agent can and will vary. Typically, the molar ratio of the compound comprising Formula (I) or (Ia) to the hydrolysis agent may range from about 1:1 to about 1:15. In a preferred embodiment, the molar ratio of the compound comprising Formula (I) or (Ia) to the hydrolysis agent may range from about 1:5 to about 1:9. In some embodiments, the molar ratio of the compound comprising Formula (I) or (Ia) to the hydrolysis agent may be about 1:5, about 1:6, about 1:7, about 1:8, or about 1:9.

The reaction mixture, as detailed herein, also includes an organic solvent. A variety of organic solvents are suitable for use in the process of the invention. Suitable organic solvents include, but are not limited to t-butyl methylether, diethylene glycol, triethylene glycol, and combinations thereof, In an exemplary embodiment, the solvent may be diethylene glycol. The weight ratio of the solvent to the compound comprising Formula (I) or (Ia) may vary. In general, the weight ratio of the solvent to the compound comprising Formula (I) or (Ia) may range from about 2:1 to about 10:1. In some embodiments, the weight ratio of the solvent to the compound comprising Formula (I) or (Ia) may be about 2:1, 3:1, 4:1, 5:1, 6:1, 7:1, 8:1, 9:1, or 10:1. In a preferred embodiment, the weight ratio of the solvent to the compound comprising Formula (I) or (Ia) may be about 5:1.

(b) Reaction Conditions

In general, the hydrolysis reaction is conducted at a temperature that ranges from about 125° C. to about 210° C. In some embodiment, the temperature of the reaction may be about 125°, 130°, 135°, 140°, 145°, 150°, 155°, 160°, 165°, 170°, 175°, 180°, 185°, 190°, 195°, 200°, 205°, or 210° C. In a preferred embodiment, the reaction may be conducted at a temperature that ranges from about 150° C. to about 200° C. The reaction is preferably performed under ambient pressure, and preferably in an inert atmosphere (e.g., nitrogen or argon).

In general, the pH of the reaction mixture will be at least about pH 12.0. In an exemplary embodiment, the pH of the reaction mixture may range from about pH 13.0 to about pH 14.0. Depending upon the hydrolysis agent, the pH of the reaction mixture also may be adjusted with an appropriate pH-modifying agent to attain the desired pH value. Those of skill in the art are familiar with suitable pH-modifying agents.

Typically, the reaction is allowed to proceed for a sufficient period of time until the reaction is complete, as determined by chromatography (e.g., HPLC). In this context, a "completed reaction" generally means that the reaction mixture contains a significantly diminished amount of the compound comprising Formula (I) or (Ia) and a significantly increased amount of the compound comprising Formula (II) or (IIa) compared to the amounts of each present at the beginning of the reaction. More specifically, the reaction generally is allowed to proceed until the level of the compound comprising Formula (II) or (IIa) no longer increases. Typically, the reaction is allowed to proceed for a period of time that ranges from about 2 hours to about 48 hours, or preferably from about 3 hours to about 12 hours. In some preferred embodiments, the duration of the reaction may be about 4.0, 4, 5, 5.0, 5.5, 6.0, 6.5, 7.0, 7.5, 8.0, 9.0, 10, 11, or 12 hours. In an exemplary embodiment, the reaction is allowed to proceed from about four to about five hours.

Upon completion of the reaction, the reaction mixture is cooled. The reaction mixture may be cooled to a temperature that ranges from about 80° C. to about 100° C., or more preferably to about 90° C. The reaction mixture also may be diluted by the addition of water. To facilitate isolation of the compound comprising Formula (II) or (IIa), the pH of the reaction mixture is typically reduced to a value ranging from about 8.0 to about 9.0, wherein the compound comprising Formula (II) or (IIa) precipitates out. Those of skill in the art will appreciate that a variety of pH lowering agents may be used to reduce the pH of the reaction mixture. Examples of suitable pH lowering agents include, but are not limited to, $H_2SO_4$, HCl, HBr, HI, $HNO_3$, $HClO_3$, $HClO_4$, $HBrO_4$, $HIO_3$, $HIO_4$, $CF_3SO_3H$, $MeSO_3H$, $H_3PO_4$, poly $H_3PO_4$, p-methyl-toluenesulfonic acid, and combinations thereof. In an exemplary embodiment, the pH of the reaction mixture may be reduced by the addition of $H_2SO_4$. The precipitated compound comprising Formula (II) or (IIa) may be easily separated from the reaction mixture using procedures well known to those of skill in the art.

The compound comprising Formula (II) or (IIa) may be further purified by recrystallization. Typically, the recrystallization is conducted in a solvent system comprising a protic solvent and an aprotic solvent. Examples of suitable protic solvents include, but are not limited to, methanol, ethanol, isopropanol, n-propanol, isobutanol, n-butanol, s-butanol, t-butanol, formic acid, acetic acid, water, and combinations thereof. Non-limiting examples of suitable aprotic solvents include acetone, acetonitrile, benzene, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), ethyl acetate, ethyl formate, ethyl methyl ketone, formamide, hexachloroacetone, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), 2-methyl tetrahydrofuran, trichloromethane, and combinations thereof. In a preferred embodiment, the solvent system comprises methanol and acetonitrile. In an exemplary embodiment, the compound comprising Formula (II) or (IIa) may be recrystallized in a 57% methanol in acetonitrile mixed solvent system. The mixture comprising the solvent system and the crude compound comprising Formula (II) or (IIa) may be heated to facilitate dissolution of the solids. The solvent may be removed from the mixture by distillation. Preferably, at least about 40% of the solvent may be removed, more preferably about 40% to about 50% of the solvent may be removed, and even more preferably, about 50% to about 55% of the solvent may be removed. Typically, the concentrated mixture is cooled to a temperature less than about 10° C. to facilitate crystallization of the compound comprising Formula (II) or (IIa).

The yield and purity of the compound comprising Formula (II) or (IIa) may vary. In general, the weight assay of the compound comprising Formula (II) or (IIa) is greater than about 90%. In one embodiment, the weight assay of the compound comprising Formula (II) or (IIa) may range from about 90% to about 95%. In another embodiment, the weight assay of the compound comprising Formula (II) or (IIa) may range from about 95% to about 99%. In a further embodiment, the weight assay of the compound comprising Formula (II) or (IIa) may be greater than about 99%. The molar yield of the conversion of the compound comprising Formula (I) or (Ia) to the compound comprising Formula (II) or (IIa) is generally at least about 65%, In general, the molar yield may range from about 65% to about 80%. In some embodiments, the molar yield may be about 65%, 66%, 67%, 68%, 69%, 70%, 71%, 72%, 73%, 74%, 75%, 76%, 77%, 78%, 79%, or 80%. In a preferred embodiment, the molar yield may range from about 65% to about 70%.

(II) Synthesis of Compounds Comprising Formula (II)

Another aspect of the invention provides a process for preparing a compound comprising Formula (II) from a compound comprising Formula (Ib). In particular, the process comprises contacting the compound comprising Formula (Ib) with a first hydrolysis agent to form the compound comprising Formula (II) and a compound comprising Formula (I). The process further comprises isolating the compound comprising Formula (I) and contacting it with a second hydrolysis agent to form additional amounts of the compound comprising Formula (II). For the purposes of illustration, Reaction Scheme 2 depicts the formation of compound comprising Formula (II) in accordance with this aspect of the invention.

Reaction Scheme 2

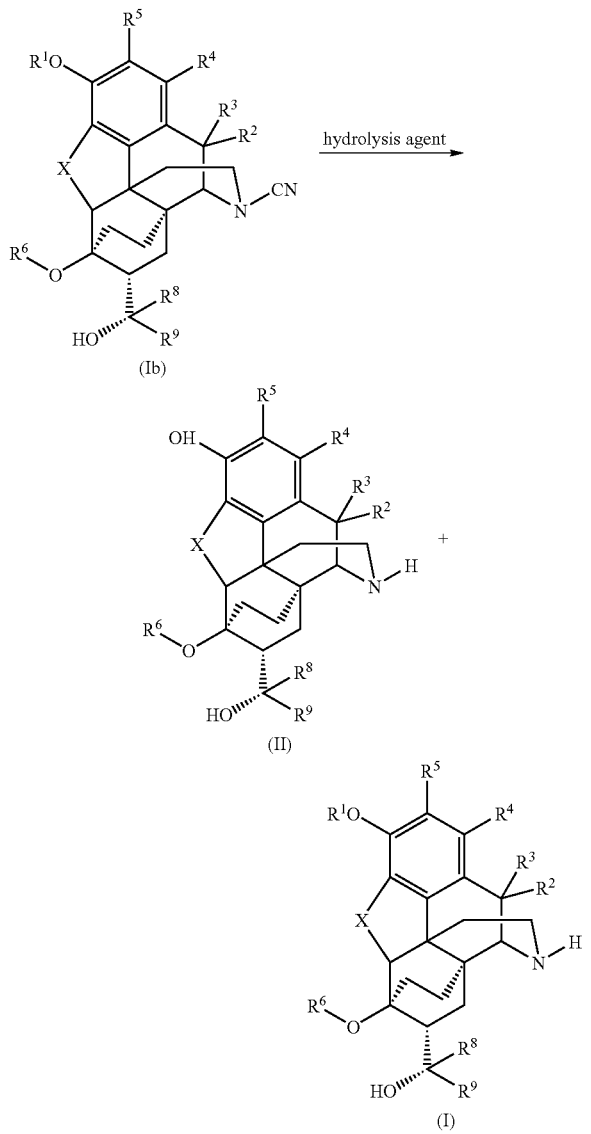

wherein:
- $R^1$, $R^7$, $R^8$, and $R^9$ are independently selected from the group consisting of hydrocarbyl and substituted hydrocarbyl;
- $R^2$ and $R^3$ are independently selected from the group consisting of hydrogen, hydrocarbyl, and substituted hydrocarbyl;
- $R^4$ and $R^5$ are independently selected from the group consisting of hydrogen, hydrocarbyl, substituted hydrocarbyl, halogen, {—}OH, {—}$NH_2$, {—}SH, {—}$SR^7$, and {—}$OR^7$;
- $R^6$ is independently selected from the group consisting of hydrogen, a protecting group, hydrocarbyl, and substituted hydrocarbyl; and
- X is a heteroatom.

In an exemplary embodiment, the compound comprising Formula (II) is norbuprenorphine, which comprises Formula (IIa), and the compound comprising Formula (I) is 3-O-methyl-norbuprenorphine, which comprises Formula (Ia):

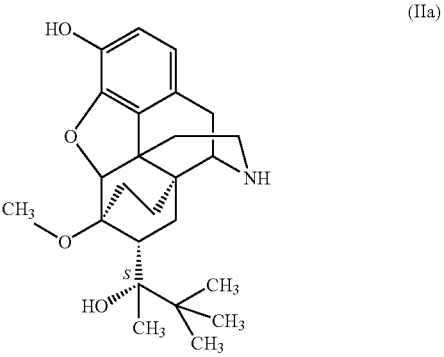

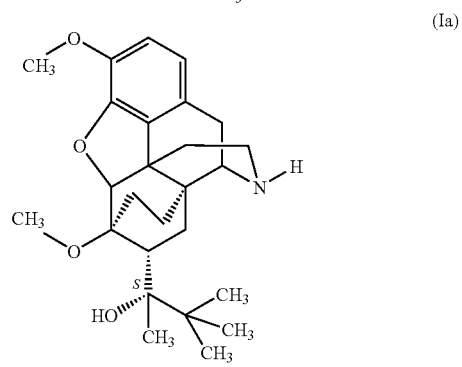

(a) Step (a) of the Process

Step (a) of the process comprises forming a reaction mixture that includes a compound comprising Formula (Ib). A variety of compounds comprising Formula (Ib) are suitable for use in the process. In one embodiment of the process, for the compound comprising Formula (Ib), $R^1$, $R^6$, $R^8$, and $R^9$ are alkyl or substituted alkyl, and X is oxygen. In an iteration of this embodiment, $R^2$, $R^3$, $R^4$, and $R^5$ are hydrogen. In another embodiment, $R^2$, $R^3$, $R^4$, and $R^5$ are hydrogen, and X is oxygen. In yet another embodiment, $R^1$ and $R^6$ are methyl. In an iteration of this embodiment, X is oxygen. In a further iteration, $R^8$ and $R^9$ are alkyl or substituted alkyl.

In an exemplary embodiment, the compound comprising Formula (Ib) is 3-O-methyl-N-cyano-buprenorphine comprising Formula (Ic):

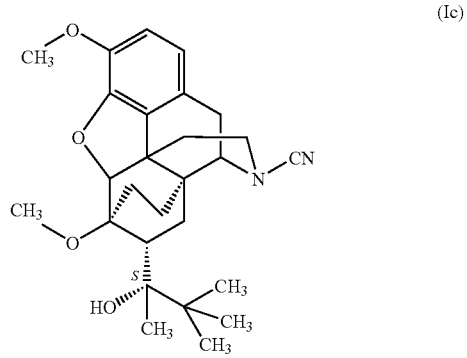

In addition to the compound comprising Formula (Ib) or (Ic), the reaction mixture also comprises a first hydrolysis agent. Suitable hydrolysis agents are detailed above in section (I)(a), In a preferred embodiment, the first hydrolysis agent may be a hydroxide of a group 1 or group 2 metal. In an exemplary embodiment, the first hydrolysis agent may be potassium hydroxide. Typically, the molar ratio of the compound comprising Formula (Ib) or (Ic) to the first hydrolysis agent may range from about 1:1 to about 1:15. In a preferred embodiment, the molar ratio of the compound comprising Formula (Ib) or (Ic) to the first hydrolysis agent may range from about 1:9 to about 1:15. In some preferred embodiments, the molar ratio of the compound comprising Formula (Ib) or (Ic) to the first hydrolysis agent may be about 1:9, 1:10, 1:11, 1:12, 1:13, 1:14, or 1:15. The reaction mixture also comprises an inorganic solvent, as detailed above in section (I)(a).

As detailed above in section (I)(b), the temperature and pH of the hydrolysis reaction may vary. In general, step (a) of the process may be conducted at a temperature that ranges from about 125° C. to about 210° C., or more preferably from about 150° C. to about 200° C. The reaction of step (a) is generally conducted at a pH of at least about 12.0, or more preferably at a pH from about 13.0 to about 14. The reaction of step (a) is allowed to proceed until the level of the compound comprising Formula (II) or (IIa) no longer increases, as detailed above in section (I)(b). Upon completion of step (a), the amount of the compound comprising Formula (I) or (Ia) in the reaction mixture may range from about 1% to about 10% by weight of the total amount of the compound comprising Formula (II) or (IIa) and the compound comprising Formula (I) or (Ia) in the reaction mixture. In some embodiments, the amount of the compound comprising Formula (I) or (Ia) in the reaction mixture may be about 1%, 2%, 3%, 4%, 5%, 6%, 7%, 8%, 9%, or 10% by weight of the total amount of compounds in the mixture, (b) Step (b) of the Process Step (b) of the process comprises isolating the compound comprising Formula (I) or (Ia) that was formed during step (a) of the process. Typically, the compound comprising Formula (I) or (Ia) is isolated by diluting the reaction mixture with water, wherein the compound comprising Formula (I) or (Ia) precipitates out of the diluted reaction mixture, but the compound comprising Formula (II) or (IIa) remains in solution. The amount of water added to the reaction mixture may vary. Typically, the weight ratio of water to the compound comprising (Ib) or (Ic) ranges from about 10:1 to about 50:1. In a preferred embodiment, the weight ratio of water to the compound comprising (Ib) or (Ic) may range from about 15:1 to about 30:1. The precipitated compound comprising Formula (I) or (Ia) may be collected using procedures known to those of skill in the art. The compound comprising (II) or (IIa) remaining in the resultant reaction mixture may be isolated by reducing the pH of the mixture, as detailed above in section (I)(b).

Step (b) of the process further comprises contacting the isolated compound comprising Formula (I) or (Ia) with a second hydrolysis agent to form additional amounts of the compound comprising Formula (II) or (IIa). Suitable hydrolysis agents are detailed above, and preferred hydrolysis agents include hydroxides of group 1 or group 1 metals. In an exemplary embodiment, the second hydrolysis agent may be potassium hydroxide. Typically, the molar ratio of the compound comprising Formula (I) or (Ia) to the second hydrolysis agent may range from about 1:1 to about 1:15. In a preferred embodiment, the molar ratio of the compound comprising Formula (I) or (Ia) to the second hydrolysis agent may range from about 1:5 to about 1:9 as detailed above in section (I)(a). Suitable organic solvents, as well as reaction conditions such as temperature and pH range are as detailed in step (a). The compound comprising Formula (II) or (IIa) formed during step (b) may be isolated and purified as detailed above in section (I)(b).

The compound comprising Formula (II) or (IIa) prepared by either process of the present invention may be an end product itself, or it may be further derivatized in one or more steps to yield further intermediates or end products. As an example, the compound comprising Formula (II) or (IIa) may undergo N-alkylation, wherein a cyclopropylmethyl group is added to form buprenorphine.

The compound comprising any of Formulas (I) or (II) may have a (−) or (+) optical activity with respect to the rotation of polarized light, based on whether the starting material used is in the (−) or (+) opiate absolute form. More specifically, each chiral center may have an R or an S configuration. For purposes of illustration, the ring atoms of a morphinan compound are numbered as diagrammed below:

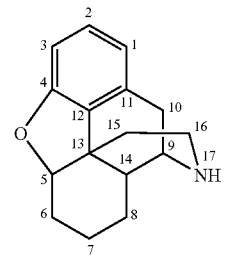

The compounds described herein may have at least six chiral centers, namely carbons C5, C6, C7, C9, C13, and C14. In general, C5 and C6 each have an R configuration, but the configuration of C7, C9, C13, and C14 may vary. The configuration of C7, C9, C13, and C14, respectively, may be may be RRSS, RSRR, SRSS, or SSRR, provided that the C15 and the C16 carbons are both either on the alpha face or the beta face of the molecule.

The invention also encompasses use of pharmaceutically acceptable salts of any of the compounds described herein. Exemplary salts include without limitation hydrochloride, hydrobromide, phosphate, sulfate, methansulfonate, acetate, formate, tartaric acid, maleic, malic, citrate, isocitrate, succinate, lactate, gluconate, glucuronate, pyruvate, oxalate, fumarate, propionate, aspartate, glutamate, benzoate, methyl fluoride, methyl chloride, methyl bromide, methyl iodide, and the like.

DEFINITIONS

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups; hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen which, subsequent to the reaction for which protection is employed, may be removed without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β methoxyethoxymethyl (MEM), tetrahydropyranyl (THP), ethoxy ethyl (EE), methylthiomethyl (MTM), 2 methoxy-2-propyl (MOP), 2 trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the following examples represent techniques discovered by the inventors to function well in the practice of the invention. Those of skill in the art should, however, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

Example 1

Synthesis of Narbuprenorphine from 3-O-Methyl-Norbuprenorphine—$1^{st}$ Run

To a Hastelloy C-276 reactor, 16.2 g of potassium hydroxide (KOH) pellets and 72.5 mL of diethylene glycol (DEG) were added. The mixture was stirred and heated (to about 80°-113° C.) to dissolve the KOH. Then 14.5 g of 3-O-methyl-norphuprenorphine was added and the reaction mixture was heated to 185° C. for 5.25 hours. The reaction mixture was cooled to about 90° C. Approximately 500 mL of deionized water was added to the reaction mixture, and the pH of the reaction mixture (~13.8) was adjusted to pH 8.6 by the addition of about 9 mL of concentrated sulfuric acid ($H_2SO_4$), and the solids were filtered off. The solids were re-slurried in water and heated to about 50-80° C. with agitation for about 1 hour. After the re-slurry cooled to room temperature, the solids were filtered off and dried. The product was analyzed by HPLC; 11.3 g of norbuprenorphine was produced, with an assay of about 90 wt/wt % and a molar yield of about 80%.

Example 2

Synthesis of Norbuprenorphine from 3-O-Methyl-Norbuprenorphine—2nd Run

KOH pellets (12.5 g) and DEG (56.15 mL) were added to a Hastelloy C-276 reactor, and the mixture was stirred and heated (to about 80°-108° C.) to dissolve the KOH. Then 11.23 g of 3-O-methyl-norphuprenorphine was added and the reaction mixture was heated to 185° C. for about 4.5 hours. The reaction mixture was cooled to about 90° C. and diluted with 500 mL of deionized water. The mixture was filtered to remove any solids, and the pH of the filtrate (~13.47) was adjusted to pH 8.66 by the addition of about 7.5 mL of sulfuric acid. The solids were filtered off and processed essentially as described in Example 1. The norbuprenorphine produced had an assay of about 92.5 wt/wt % and a molar yield of 73%.

Example 3

Synthesis of Norbuprenorphine from 3-O-Methyl-Norbuprenorphine—3rd Run

KOH pellets (6.95 g) and DEG (52.9 mL) were added to a Hastelloy C-276 reactor, and the mixture was stirred and heated (to about 90°-118° C.). Then 10.58 g of 3-O-methyl-norphuprenorphine was added and the reaction mixture was heated to 185° C. for about 4 hours. The reaction mixture was cooled to about 90° C., diluted with 300 mL of deionized water, stirred for several minutes, and then another 300 mL of water was added. The pH of the mixture (~12.80) was adjusted to pH 8.04 by the addition of about 3 mL of concentrated sulfuric acid. The solids were filtered off and processed essentially as described in Example 1. The norbuprenorphine produced had an assay of 91.0 wt/wt % and a molar yield of 65%.

What is claimed is:

1. A process for the preparation of a compound of Formula (II), the process comprising contacting a compound of Formula (I) with a hydrolysis agent to form the compound of Formula (II):

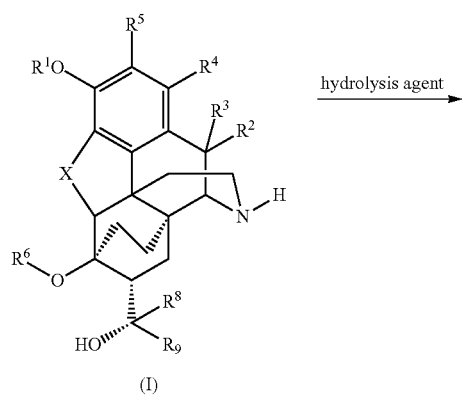

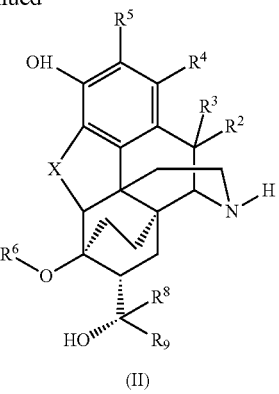

wherein:
$R^1$, $R^7$, $R^8$, and $R^9$ are independently selected from the group consisting of hydrocarbyl and substituted hydrocarbyl;
$R^2$, and $R^3$ are independently selected from the group consisting of hydrogen, hydrocarbyl and substituted hydrocarbyl;
$R^4$ and $R^5$ are independently selected from the group consisting of hydrogen, hydrocarbyl, substituted hydrocarbyl, halogen, {—}OH, {—}NH$_2$, {—}SH, {—}SR$^7$, and {—}OR$^7$;
$R^6$ is independently selected from the group consisting of hydrogen, a protecting group, hydrocarbyl, and substituted hydrocarbyl; and
X is oxygen, and
wherein the molar ratio of the compound of Formula (I) to the hydrolysis agent is from about 1:5 to about 1:9 and wherein the molar yield of Formula (II) is at least 65%.

2. The process of claim 1, wherein $R^1$, $R^6$, $R^8$, and $R^9$ are alkyl or substituted alkyl; and $R^2$, $R^3$, $R^4$, and $R^5$ are hydrogen.

3. The process of claim 1, wherein the hydrolysis agent is a compound having a pKa of greater than about 12.0.

4. The process of claim 1, wherein $R^1$, $R^6$, $R^8$, and $R^9$ are alkyl or substituted alkyl; the hydrolysis agent is a hydroxide of a group 1 or group 2 metal; the reaction is conducted in the presence of an organic solvent; the reaction is conducted at a pH of at least about 12.0; and the reaction is conducted at a temperature from about 150° C. to about 200° C.

5. The process of claim 4, wherein the hydrolysis agent is potassium hydroxide.

6. The process of claim 1, wherein the optical activity of the compound of Formula (I) or (II) is selected from the group consisting of (+), (−), and combinations thereof; the configuration of each of C5 and C6 is R; and the configuration of C7, C9, C13, and C14, respectively, is selected from the group consisting of may be RRSS, RSRR, SRSS, and SSRR, provided that the C15 and the C16 carbons are both either on the alpha face or the beta face of the molecule.

7. A process for the preparation of a compound of Formula (IIa), the process comprising contacting a compound of Formula (Ia) with a hydrolysis agent to form the compound of Formula (IIa):

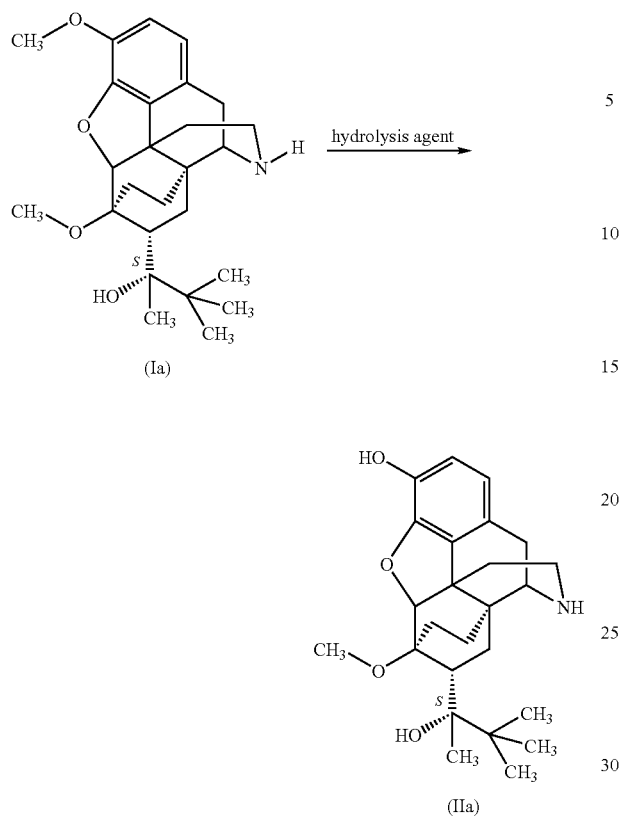

(Ia)

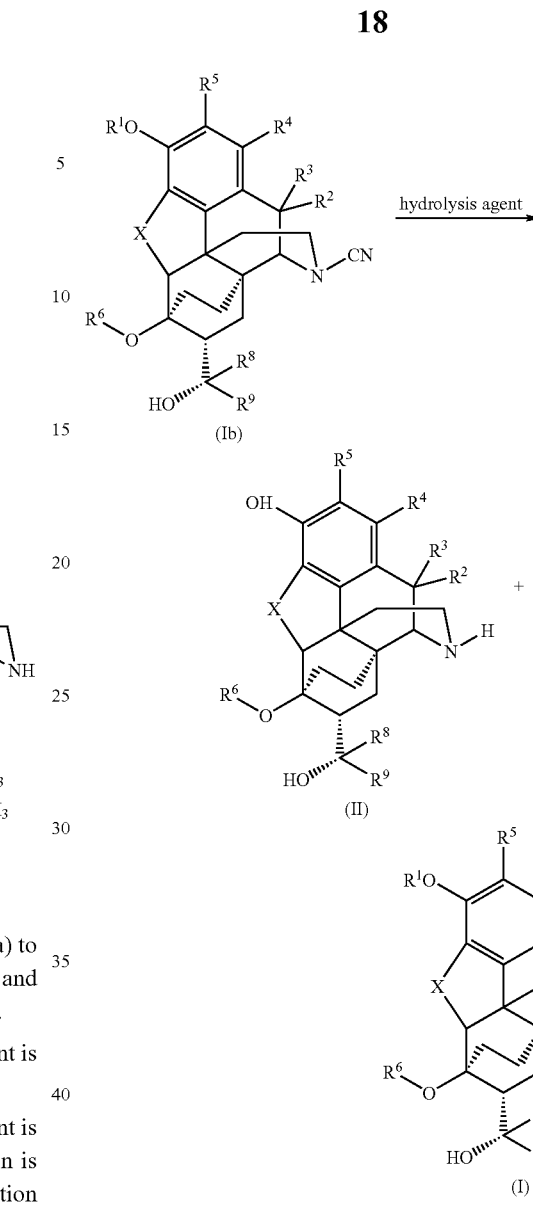

(Ib)

(IIa)

(II)

(I)

wherein the molar ratio of the compound of Formula (Ia) to the hydrolysis agent is from about 1:5 to about 1:9 and wherein the molar yield of Formula (IIa) is at least 65%.

8. The process of claim 7, wherein the hydrolysis agent is a compound having a pKa of greater than about 12.0.

9. The process of claim 7, wherein the hydrolysis agent is a hydroxide of a group 1 or group 2 metal; the reaction is conducted in the presence of an organic solvent; the reaction is conducted at a pH of at least about 12.0; and the reaction is conducted at a temperature from about 150° C. to about 200° C.

10. The process of claim 9, wherein the hydroxide is potassium hydroxide.

11. The process of claim 7, wherein the optical activity of the compound of Formulas (Ia) or (IIa) is selected from the group consisting of (+), (−), and combinations thereof; the configuration of each of C5 and C6 is R; and the configuration of C7, C9, C13, and C14, respectively, is selected from the group consisting of may be RRSS, RSRR, SRSS, and SSRR, provided that the C15 and the C16 carbons are both either on the alpha face or the beta face of the molecule.

12. A process for the preparation of a compound of Formula (II), the process comprising:
a) contacting a compound of Formula (Ib) with a first hydrolysis agent to form the compound of Formula (II) and a compound of Formula (I):

wherein:
R$^1$, R$^7$, R$^8$, and R$^9$ are independently selected from the group consisting of hydrocarbyl and substituted hydrocarbyl;
R$^2$ and R$^3$ are independently selected from the group consisting of hydrogen, hydrocarbyl, and substituted hydrocarbyl;
R$^4$ and R$^5$ are independently selected from the group consisting of hydrogen, hydrocarbyl, substituted hydrocarbyl, halogen, {—}OH, {—}NH$_2$, {—}SH, {—}SR$^7$, and {—}R$^7$;
R$^6$ is independently selected from the group consisting of hydrogen, a protecting group, hydrocarbyl, and substituted hydrocarbyl; and X is oxygen; and
b) isolating the compound of Formula (I); and
c) contacting the isolated compound of Formula (I) with a second hydrolysis agent to form additional amounts of the compound of Formula (II), wherein the molar ratio of the compound of Formula (Ib) to the first hydrolysis agent is from about 1:9 to about 1:15 and the molar ratio of the compound of Formula (I) to the second hydrolysis agent is from about 1:5 to about 1:9.

13. The process of claim 12, wherein $R^1$, $R^6$, $R^8$, and $R^9$ are alkyl or substituted alkyl; and $R^2$, $R^3$, $R^4$, and $R^5$ are hydrogen.

14. The process of claim 12, wherein the first and second hydrolysis agents are each a compound having a pKa of greater than about 12.0.

15. The process of claim 12 wherein $R^1$, $R^6$, $R^8$, and $R^9$ are alkyl or substituted alkyl; the first and second hydrolysis agents are each a hydroxide of a group 1 or group 2 metal; the reactions in steps (a), (b) and (c) are conducted in the presence of an organic solvent; the reaction in step (b) further comprises an addition of water; the reactions in steps (a), (b) and (c) are conducted at a pH of at least about 12.0; and the reactions in steps (a) and (b) are conducted at a temperature from about 150° C. to about 200° C.

16. The process of claim 12, wherein the amount of the compound of Formula (I) formed is from about 1% to about 10% by weight of the total amount of the compound of Formula (II) and the compound of Formula (I) formed in step (a); and the molar yield of the compound of Formula (II) in step (a) is greater than about 70%; and the molar yield of the compound of Formula (II) in step (c) is greater than about 70%.

17. The process of claim 12, wherein the optical activity of the compound of Formulas (I), (Ib), or (II) is selected from the group consisting of (+), (-), and combinations thereof; the configuration of each of C5 and C6 is R; and the configuration of C7, C9, C13, and C14, respectively, is selected from the group consisting of may be RRSS, RSRR, SRSS, and SSRR, provided that the C15 and the C16 carbons are both either on the alpha face or the beta face of the molecule.

18. A process for the preparation of a compound of Formula (IIa), the process comprising:
a) contacting a compound of Formula (Ic) with a first hydrolysis agent to form the compound of Formula (IIa) and a compound of Formula (Ia):

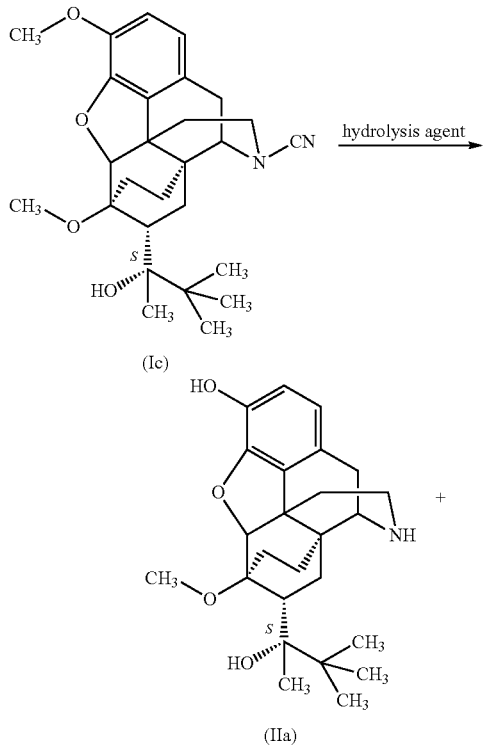

b) isolating the compound of Formula (Ia); and
c) contacting the isolated compound of Formula (Ia) with a second hydrolysis agent to form additional amounts of the compound of Formula (IIa), wherein the molar ratio of the compound of Formula (Ic) to the first hydrolysis agent is from about 1:9 to about 1:15 and the molar ratio of the compound of Formula (Ia) to the second hydrolysis agent is from about 1:5 to about 1:9.

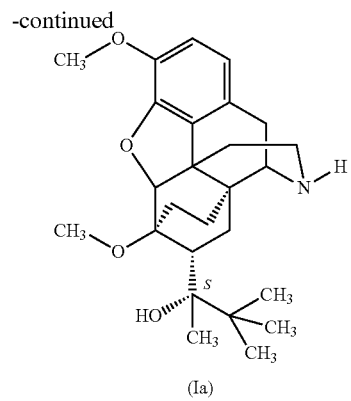

19. The process of claim 18, wherein the first and second hydrolysis agents are each a compound having a pKa of greater than about 12.0.

20. The process of claim 18, wherein the first and second hydrolysis agents are each a hydroxide of a group 1 or group 2 metal; the reactions in steps (a), (b) and (c) are conducted in the presence of an organic solvent; the reaction of step (b) further comprises an addition of water; the reactions in steps (a), (b) and (c) are conducted at a pH of at least about 12.0; and the reactions in steps (a) and (c) are conducted at a temperature from about 150° C. to about 200° C.

21. The process of claim 20, wherein the first and second hydrolysis agents are each potassium hydroxide.

22. The process of claim 18, wherein the amount of the compound of Formula (Ia) formed is from about 1% to about 10% by weight of the total amount of the compound of Formula (IIa) and the compound comprising Formula (Ia) formed in step (a); and the molar yield of the compound of Formula (IIa) in step (a) is greater than about 70% and the molar yield of compound of Formula (IIa) in step (c) is greater than 70%.

23. The process of claim 18, wherein the optical activity of the compound of Formulas (Ia), (Ic), or (IIa) is selected from the group consisting of (+), (-), and combinations thereof; the configuration of each of C5 and C6 is R; and the configuration of C7, C9, C13, and C14, respectively, is selected from the group consisting of may be RRSS, RSRR, SRSS, and SSRR, provided that the C15 and the C16 carbons are both either on the alpha face or the beta face of the molecule.

* * * * *